US011273271B2

(12) United States Patent
Fink et al.

(10) Patent No.: US 11,273,271 B2
(45) Date of Patent: Mar. 15, 2022

(54) AEROSOLIZATION SYSTEM WITH FLOW RESTRICTOR AND FEEDBACK DEVICE

(71) Applicant: Aerami Therapeutics, Inc., Durham, NC (US)

(72) Inventors: Jim Fink, Brisbane, CA (US); Lisa Molloy, Brisbane, CA (US); Ronan MacLoughlin, Galway (IE); Claire Elizabeth Lillis, Galway (IE); Michael Joseph Casey, CorrnaMona (IE); John Matthew Mullins, Tuam (IE); Kieran James Hyland, Galway (IE); Joseph Martin Grehan, Gort (IE)

(73) Assignee: Aerami Therapeutics, Inc., Durham, NC (US)

( * ) Notice: Subject to any disclaimer, the term of this patent is extended or adjusted under 35 U.S.C. 154(b) by 792 days.

(21) Appl. No.: 15/670,981

(22) Filed: Aug. 7, 2017

(65) Prior Publication Data

US 2018/0021530 A1 Jan. 25, 2018

Related U.S. Application Data

(63) Continuation-in-part of application No. 14/743,763, filed on Jun. 18, 2015, now Pat. No. 10,471,222.
(Continued)

(51) Int. Cl.
*A61M 15/00* (2006.01)
*A61M 11/00* (2006.01)
*A61M 16/00* (2006.01)

(52) U.S. Cl.
CPC ...... *A61M 15/0085* (2013.01); *A61M 11/005* (2013.01); *A61M 15/002* (2014.02);
(Continued)

(58) Field of Classification Search
CPC .......... A61M 15/0085; A61M 15/0021; A61M 2205/3334; A61M 2205/3382;
(Continued)

(56) References Cited

U.S. PATENT DOCUMENTS 3,789,843 A 2/1974 Armstronq et al.
4,564,129 A 1/1986 Urban et al.
(Continued)

FOREIGN PATENT DOCUMENTS

EP 2 724 741 A1 4/2014
RU 2383358 C2 10/2010
(Continued)

OTHER PUBLICATIONS

U.S. Appl. No. 14/743,763 received a Non-Final Office Action dated Oct. 5, 2018, 14 pages.
(Continued)

*Primary Examiner* — Kendra D Carter
*Assistant Examiner* — Jonathan S Paciorek
(74) *Attorney, Agent, or Firm* — Kilpatrick Townsend & Stockton LLP

(57) ABSTRACT

In one aspect, embodiments of the present invention provide an aerosolization device for ensuring proper delivery of an aerosolized medication to a user's respiratory system. The aerosolization device may include a conduit, an aerosol generator, a restrictor disposed within the conduit, and an indicator mechanism. The conduit may include a mouthpiece end by which a user may cause inspiratory flow through the conduit. The aerosol generator may include a vibratable mesh. The restrictor may define a plurality of apertures disposed along an outer periphery of the restrictor configured to provide an increase in pressure differential that varies with an inspiratory flow rate within the conduit and to provide a relatively laminar flow downstream of the restric-
(Continued)

tor compared to upstream of the restrictor. The indicator mechanism may indicate to a user a state of a parameter of the inspiratory flow relative to a predefined desired range.

20 Claims, 16 Drawing Sheets

Related U.S. Application Data

(60) Provisional application No. 62/019,791, filed on Jul. 1, 2014.

(52) U.S. Cl.
CPC ... *A61M 15/0021* (2014.02); *A61M 2016/003* (2013.01); *A61M 2016/0021* (2013.01); *A61M 2016/0027* (2013.01); *A61M 2205/3331* (2013.01); *A61M 2205/3334* (2013.01); *A61M 2205/3382* (2013.01); *A61M 2205/3386* (2013.01); *A61M 2205/502* (2013.01); *A61M 2205/52* (2013.01); *A61M 2205/581* (2013.01); *A61M 2205/582* (2013.01); *A61M 2205/584* (2013.01); *A61M 2205/587* (2013.01); *A61M 2205/6018* (2013.01); *A61M 2205/6054* (2013.01); *A61M 2205/6072* (2013.01); *A61M 2205/8206* (2013.01); *A61M 2206/11* (2013.01)

(58) Field of Classification Search
CPC .... A61M 2205/3386; A61M 2205/584; A61M 2205/587
See application file for complete search history.

(56) References Cited

U.S. PATENT DOCUMENTS

| | | | |
|---|---|---|---|
| 5,060,642 A | 10/1991 | Gilman | |
| 5,134,993 A | 8/1992 | Van Der Linden et al. | |
| 5,152,456 A * | 10/1992 | Ross | A61M 15/0085 239/102.2 |
| 5,164,740 A | 11/1992 | Ivri | |
| 5,320,094 A | 6/1994 | Laube et al. | |
| 5,333,106 A | 7/1994 | Lanpher et al. | |
| 5,347,998 A | 9/1994 | Hodson et al. | |
| 5,363,842 A | 11/1994 | Mishelevich et al. | |
| 5,364,838 A | 11/1994 | Rubsamen | |
| 5,474,059 A | 12/1995 | Cooper | |
| 5,479,920 A | 1/1996 | Piper et al. | |
| 5,497,944 A * | 3/1996 | Weston | A61M 15/0065 239/321 |
| 5,515,842 A | 5/1996 | Ramseyer et al. | |
| 5,586,550 A | 12/1996 | Ivri et al. | |
| 5,655,520 A | 8/1997 | Howe et al. | |
| 5,672,581 A | 9/1997 | Rubsamen et al. | |
| 5,743,250 A | 4/1998 | Gonda et al. | |
| 5,758,637 A | 6/1998 | Ivri et al. | |
| 5,759,101 A | 6/1998 | Von Kohorn | |
| 5,884,620 A | 3/1999 | Gonda et al. | |
| 5,915,378 A | 6/1999 | Lloyd et al. | |
| 5,938,117 A | 8/1999 | Ivri | |
| 5,941,240 A | 8/1999 | Gonda et al. | |
| 5,957,124 A | 9/1999 | Lloyd et al. | |
| 6,014,970 A | 1/2000 | Ivri et al. | |
| 6,085,740 A | 7/2000 | Ivri et al. | |
| 6,085,753 A | 7/2000 | Gonda et al. | |
| 6,089,260 A | 7/2000 | Jaworski et al. | |
| 6,098,615 A | 8/2000 | Lloyd et al. | |
| 6,109,261 A | 8/2000 | Clarke et al. | |
| 6,131,567 A | 10/2000 | Gonda et al. | |
| 6,166,496 A * | 12/2000 | Lys | H05B 45/20 315/316 |
| 6,205,999 B1 | 3/2001 | Ivri et al. | |
| 6,312,665 B1 | 11/2001 | Modi | |
| 6,408,854 B1 | 6/2002 | Gonda et al. | |
| 6,427,682 B1 | 8/2002 | Klimowicz et al. | |
| 6,467,476 B1 | 10/2002 | Ivri et al. | |
| 6,534,701 B2 | 3/2003 | Isozaki | |
| 6,540,153 B1 | 4/2003 | Ivri | |
| 6,540,154 B1 | 4/2003 | Ivri | |
| 6,543,701 B1 | 4/2003 | Ho | |
| 6,629,646 B1 | 10/2003 | Ivri | |
| 6,640,804 B2 | 11/2003 | Ivri et al. | |
| 6,647,987 B2 | 11/2003 | Gonda et al. | |
| 6,655,379 B2 | 12/2003 | Clark et al. | |
| 6,681,762 B1 | 1/2004 | Scheuch et al. | |
| 6,688,304 B2 | 2/2004 | Gonda et al. | |
| 6,755,189 B2 | 6/2004 | Ivri et al. | |
| 6,814,071 B2 | 11/2004 | Klimowicz et al. | |
| 6,904,908 B2 | 6/2005 | Bruce et al. | |
| 6,921,020 B2 | 7/2005 | Ivri | |
| 6,926,208 B2 | 8/2005 | Ivri | |
| 6,978,941 B2 | 12/2005 | Litherland et al. | |
| 7,028,686 B2 | 4/2006 | Gonda et al. | |
| 7,032,590 B2 | 4/2006 | Loeffler et al. | |
| 7,040,549 B2 | 5/2006 | Ivri et al. | |
| 7,047,964 B2 * | 5/2006 | Bacon | A61M 15/0091 128/200.23 |
| 7,066,398 B2 | 6/2006 | Borland et al. | |
| 7,083,112 B2 | 8/2006 | Ivri | |
| 7,100,600 B2 | 9/2006 | Loeffler et al. | |
| 7,108,197 B2 | 9/2006 | Ivri | |
| 7,131,440 B2 | 11/2006 | Sonntag | |
| 7,174,888 B2 | 2/2007 | Ivri et al. | |
| 7,185,651 B2 | 3/2007 | Alston et al. | |
| 7,195,011 B2 | 3/2007 | Loeffler et al. | |
| 7,219,664 B2 | 5/2007 | Ruckdeschel | |
| 7,364,571 B2 | 4/2008 | Schinazi et al. | |
| 7,448,375 B2 | 11/2008 | Gonda et al. | |
| 7,451,760 B2 | 11/2008 | Denyer et al. | |
| 7,600,512 B2 | 10/2009 | Lee et al. | |
| 7,628,339 B2 | 12/2009 | Ivri et al. | |
| 7,683,029 B2 | 3/2010 | Hindle et al. | |
| 7,748,382 B2 | 7/2010 | Denyer et al. | |
| 7,819,115 B2 | 10/2010 | Sexton et al. | |
| 7,891,358 B2 | 2/2011 | Kolb et al. | |
| 7,913,688 B2 * | 3/2011 | Cross | A61M 11/041 128/203.26 |
| 8,082,918 B2 | 12/2011 | Jansen et al. | |
| 8,950,394 B2 | 2/2015 | Patton et al. | |
| 9,004,061 B2 | 4/2015 | Patton et al. | |
| 9,171,283 B2 | 10/2015 | Curbera et al. | |
| 2001/0037805 A1 | 11/2001 | Gonda et al. | |
| 2001/0039948 A1 | 11/2001 | Sexton et al. | |
| 2003/0019493 A1 | 1/2003 | Narayan et al. | |
| 2003/0047620 A1 | 3/2003 | Litherland et al. | |
| 2004/0134494 A1 | 7/2004 | Papania et al. | |
| 2005/0011514 A1 | 1/2005 | Power et al. | |
| 2006/0239930 A1 | 10/2006 | Lamche et al. | |
| 2007/0113841 A1 | 5/2007 | Fuchs | |
| 2007/0144514 A1 * | 6/2007 | Yeates | A61M 15/0086 128/203.15 |
| 2007/0163572 A1 | 7/2007 | Addington et al. | |
| 2007/0240712 A1 * | 10/2007 | Fleming | A61M 15/0028 128/203.15 |
| 2008/0029083 A1 | 2/2008 | Masada et al. | |
| 2008/0060641 A1 | 3/2008 | Smith et al. | |
| 2008/0233053 A1 | 9/2008 | Gross et al. | |
| 2008/0257337 A1 * | 10/2008 | Denyer | A61M 11/005 128/200.14 |
| 2009/0056708 A1 | 3/2009 | Stenzler et al. | |
| 2009/0157037 A1 | 6/2009 | Iyer et al. | |
| 2009/0241946 A1 | 10/2009 | Clancy et al. | |
| 2009/0301472 A1 | 12/2009 | Kim et al. | |
| 2010/0075001 A1 | 3/2010 | Succar. et al. | |
| 2010/0078015 A1 | 4/2010 | Imran | |
| 2010/0154794 A1 | 6/2010 | Valentin | |
| 2010/0319686 A1 | 12/2010 | Schennum | |
| 2011/0114089 A1 | 5/2011 | Andersen et al. | |
| 2011/0168172 A1 | 7/2011 | Patton et al. | |
| 2011/0226242 A1 | 9/2011 | von Hollen et al. | |
| 2012/0041381 A1 | 2/2012 | Raj et al. | |

(56) References Cited

U.S. PATENT DOCUMENTS

| | | | |
|---|---|---|---|
| 2012/0048268 A1 | 3/2012 | Hyun et al. | |
| 2012/0285236 A1* | 11/2012 | Haartsen | A61M 11/005 |
| | | | 73/204.11 |
| 2013/0053719 A1* | 2/2013 | Wekell | A61B 5/09 |
| | | | 600/539 |
| 2013/0269684 A1 | 10/2013 | Patton et al. | |
| 2013/0269694 A1 | 10/2013 | Patton et al. | |
| 2014/0041653 A1 | 2/2014 | Patton et al. | |
| 2014/0318533 A1 | 10/2014 | Patton et al. | |
| 2015/0048119 A1 | 2/2015 | Boehm et al. | |

FOREIGN PATENT DOCUMENTS

| | | |
|---|---|---|
| WO | 1992/11050 A1 | 7/1992 |
| WO | 1998/022290 A1 | 5/1998 |
| WO | 2003/030829 A2 | 4/2003 |
| WO | 2004/028608 A1 | 4/2004 |
| WO | 2006/062449 A1 | 6/2006 |
| WO | 2007/047948 A2 | 4/2007 |
| WO | 2012/026963 A2 | 3/2012 |
| WO | 2013/098334 A1 | 7/2013 |

OTHER PUBLICATIONS

Clark; 2012 "Understanding Penetration Index Measurements and Regional Lung Targeting" Journal of Aerosol Medicine and Pulmonary Drug Delivery, 25(4), 179-187.
Liu, F—Y, "Pulmonary Delivery Of Free Liposomal Insulin, " Pharmaceutical Research, Kluwer Academic Publishers, New York, NY, vol. 10, No. 2, Feb. 1, 1993, 5 pages.
International Search Report and Written Opinion of PCT/US2015/037505 dated Sep. 29, 2015, 10 pages.
International Preliminary Report on Patentability of PCT/US2015/037505, dated Jan. 12, 2017, 8 pages.
International Search Report and Written Opinion of PCT/US2011/020926 dated Mar. 14, 2011, 11 pages.
International Search Report and Written Opinion of PCT/US2011/020925 dated Mar. 14, 2011, 7 pages.
International Search Report and Written Opinion of PCT/US2013/034359 dated Jun. 28, 2013, 35 pages.
European Search Report of EP 11733287 dated Jul. 12, 2013, 12 pages.
EP Application No. 15816007.7 received and Extended European Search Report dated Jan. 26, 2018, 8 pages.
Russian Application No. 2017103007 received an Office Action dated Jan. 17, 2019, 16 pages.
U.S. Appl. No. 14/743,763 received a Final Office Action dated Mar. 6, 2019, 12 pages.
Kikoin I.K. "Physics for 8th grade", Textbook. 4th edition, revised.—M.: Prosveshcheniye, 1973, p. 236.
Savelyev I.V., "Physics: A General Course, vol. 1. Mechanics. Molecular Physics", Textbook, 2nd edition, revised, M.: Nauka. Chief editorial board of physical and mathematical literature, 1982, p. 255.
CN201580046560.3 received an Office Action dated Mar. 29, 2019, 6 pages.
RU2017103007 received an Office Action dated Apr. 26, 2019, 19 pages.
James, et al., Annexe D. Deposition of Inhaled Particles, Annals of the ICRP, vol. 24, Issues 1-3, Sep. 1, 1994, pp. 231-299.
Pruisner et al., "Snow, Rain, and the Stokes Number". APA, 2008, 4 pages.
Stahlhofen, et al., "Intercomparison of Experimental Regional Aerosol Deposition Data", Journal of Aerosol Medicine, vol. 2, No. 3, Jun. 9, 1989, 99 285-326.
Weers, et al., "The Impact of Inspiratory Flow Rate on Drug Delivery to the Lungs with Dry Powder Inhalers", Pharm Res, (2017) 34:507-258, published online, Oct. 13, 2016.
Brazil Application No. BR112016030805-0 received an Office Action dated May 5, 2020, 7 pages, 3 pages English Translation, 4 pages Original Office Action.

\* cited by examiner

AEROSOLIZATION SYSTEM WITH FLOW RESTRICTOR AND FEEDBACK DEVICE

CROSS REFERENCE TO RELATED APPLICATIONS

This application is a continuation-in-part of U.S. patent application Ser. No. 14/743,763, filed on Jun. 18, 2015, entitled "AEROSOLIZATION SYSTEM WITH FLOW RESTRICTOR AND FEEDBACK DEVICE," which claims the benefit of U.S. Provisional Application No. 62/019,791, filed on Jul. 1, 2014, entitled "AEROSOLIZATION SYSTEM WITH FLOW RESTRICTOR AND FEEDBACK DEVICE," the entire disclosures of which are hereby incorporated by reference, for all purposes, as if fully set forth herein.

BACKGROUND OF THE INVENTION

Aerosolization systems provide effective delivery for a variety of medicaments, such as insulin and asthma medications. Such systems deliver the medicaments directly to a user's respiratory system by aerosolizing a desired dose of the medicament in liquid form. The user then inhales the aerosolized medicament directly into the respiratory system, enabling faster treatment of various medical conditions.

Delivery of accurate and consistent metered doses of aerosolized medicament to a user is very important. Current aerosolization systems often provide inconsistent doses by allowing some of the medicament to remain in a reservoir in liquid form after the aerosolization process is completed. Additionally, the aerosolized medicament is often delivered with too great or too little force for substantially all of the metered dose to properly enter the user's respiratory system. A further problem of current aerosolization systems is a tendency for the medicament to become contaminated by the user or other sources. Contamination of the medicament is particularly problematic since some or all of the contaminated medicament is thereafter delivered directly to the user's respiratory system after aerosolization. Embodiments of the invention may provide solutions to these and other problems.

BRIEF SUMMARY OF THE INVENTION

According to one aspect, a method of operating an inhaler comprises receiving a dose of liquid medicament onto a vibratable mesh, and measuring a flowrate of air flowing through the inhaler, the flow of air resulting from an inhalation by a user of the inhaler. The method further comprises actuating a vibratable element to vibrate the mesh, causing aerosolization of liquid medicament and creating a plume of aerosolized liquid medicament in the flowing air. The method further comprises, when the flowrate is between a first threshold value and a second threshold value greater than the first, continuing to vibrate the mesh and providing a first indication to the user of the inhaler indicating that the flowrate is in a desired range between the first and second threshold values. When the flowrate exceeds the second threshold value, vibration of the mesh is stopped and a second indication is provided to the user of the inhaler indicating that the flowrate is above the desired range. When the flowrate falls below the first threshold value during aerosolization of the liquid medicament, vibration of the mesh is stopped and a third indication is provided to the user of the inhaler indicating that the flowrate is below the desired range. The method further comprises, after substantially the entire amount of liquid medicament received onto the mesh has been aerosolized, providing a fourth indication to the user of the inhaler indicating that dosage is complete. In some embodiments, the first, second, third, and fourth indications are visual indications. In some embodiments, the first, second, third, and fourth indications are provided via illumination of one or more lights, and include one or more indicators selected from the group consisting of light of a particular color, a constantly-illuminated light, a flashing light, a light the flashes at different rates for different indications, and a light that changes color. In some embodiments, the first threshold value is about 7 L/min and the second threshold value is about 14 L/min. In some embodiments, the method further comprises providing the third indication before the flowrate has reached the first threshold value. In some embodiments, the first indication is constantly-illuminated light of a first color, the second indication is light flashing at a first rate, the third indication is light flashing at a second rate slower than the first rate, and the fourth indication is light of a second color different from the first. In some embodiments, the first, second, third, and fourth indications are all provided by a single multi-color light emitting diode. In some embodiments, the method further comprises, when aerosolization of the dose of medicament is completed during an inhalation by the user of the inhaler, delaying the fourth indication. In some embodiments, more than one inhalation by the user of the inhaler is required to achieve aerosolization of substantially the entire dose of liquid medicament.

In another aspect, a method for operating an inhaler comprises receiving a dose of liquid medicament onto a mesh, and measuring a flowrate of air flowing through the inhaler, the flow of air resulting from an inhalation by a user of the inhaler. The method further comprises actuating a vibratable element to vibrate the mesh, causing aerosolization of liquid medicament from the liquid medicament dose and creating a plume of aerosolized liquid medicament in the flowing air. The method further comprises, when the flowrate is between 7 L/min and 14 L/min, continuing to vibrate the mesh and constantly illuminating a light that is visible to the user of the inhaler and, when the flowrate exceeds 14 L/min, stopping vibration of the mesh and causing the light to flash. In some embodiments, the method further comprises, when the flowrate falls below 7 L/min during aerosolization of the liquid medicament, stopping vibration of the mesh and causing the light flash more slowly than when the flow rate is above 14 L/min. In some embodiments, the method further comprises, after substantially the entire amount of liquid medicament received onto the mesh has been aerosolized, generating constantly-illuminated light of a different color than when the flow rate is between 7 and 14 L/min.

In another aspect, an aerosolization system comprises a housing defining a mouthpiece and a liquid receptacle fluidly coupled to the mouthpiece, wherein the liquid receptacle defines an opening configured to receive a dosage of liquid, and an aerosol generator disposed within the housing. The aerosol generator comprises a mesh and a vibratable element configured to vibrate the mesh to turn the dosage of liquid into an aerosol. The aerosolization system further comprises a flow sensor configured to detect a flowrate of the air through the mouthpiece, one or more lights visible to a user of the inhaler during use, and a controller coupled to the one or more lights, the flow sensor, and the vibratable element. The controller is configured to, when the flowrate is between a first threshold value and a second threshold value greater than the first, vibrate the mesh and provide a first indication using one of the one or more lights to the user of the inhaler indicating that the flowrate is in a desired range between the first and second threshold values; when the flowrate exceeds the second threshold value, stop vibration of the mesh and provide a second indication using one of the one or more lights to the user of the inhaler indicating that the flowrate is above the desired range; when the flowrate falls below the first threshold value during aerosolization of the liquid medicament, stop vibration of the mesh and provide a third indication using one of the one or more lights to the user of the inhaler indicating that the flowrate is below the desired range; and after substantially the entire amount of liquid medicament received onto the mesh has been aerosolized, provide a fourth indication to the user of the inhaler indicating that dosage is complete. In some embodiments, the first threshold value is 7 L/min and the second threshold value is 14 L/min. In some embodiments, the first indication is a constantly-illuminated light of a first color, the second indication is a light flashing at a first rate, the third indication is a light flashing at a second rate slower than the first rate is, and the fourth indication is a light of a second color different from the first.

BRIEF DESCRIPTION OF THE DRAWINGS

The present invention is described in conjunction with the appended figures.

Figure 1A:
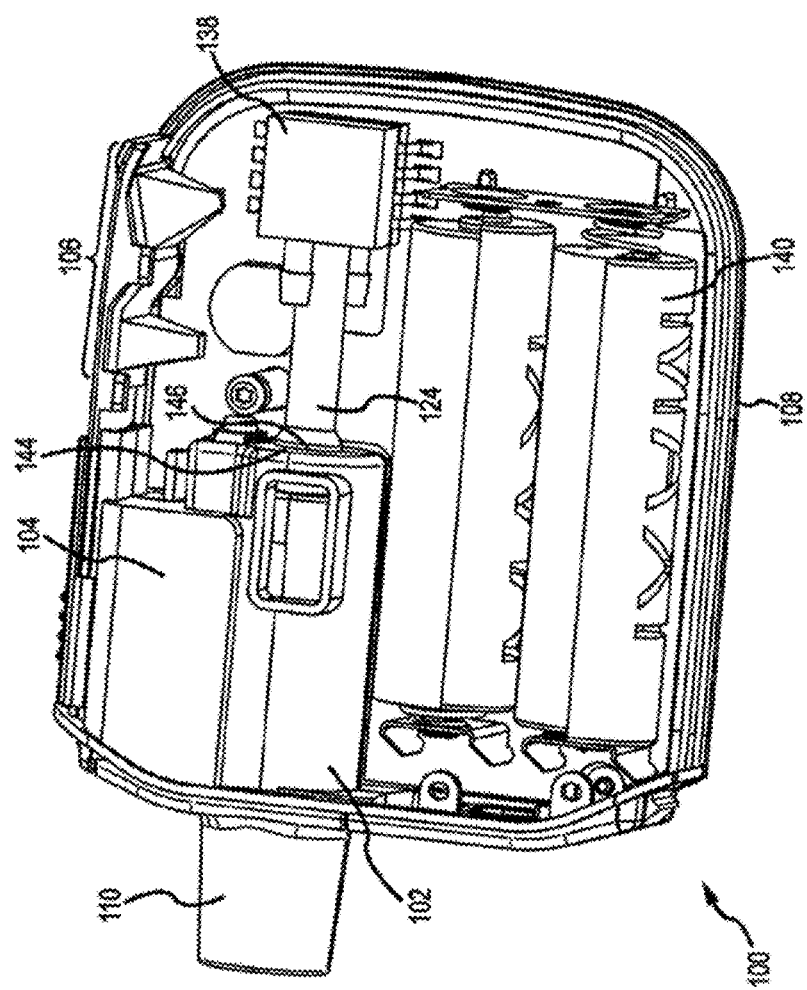
FIG. 1A depicts an interior of an aerosolization device according to embodiments of the invention.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

The ensuing description provides exemplary embodiments only, and is not intended to limit the scope, applicability or configuration of the invention. Rather, the ensuing description of exemplary embodiments will provide those skilled in the art with an enabling description for implementing various embodiments of the invention. It will be understood that various changes may be made in the function and arrangement of elements without departing from the spirit and scope of the invention as set forth in the appended claims. For example, any detail discussed with regard to one embodiment may or may not be present in variations of that embodiment, and/or in other embodiments discussed herein.

Embodiments of an aerosolization device for assisting in proper delivery of an aerosolized medication to a user's respiratory system are described herein. In many embodiments, liquid medicament may be provided to an aerosolization device in a metered dose. The liquid medicament may be dispensed to an aerosol generator. In some embodiments, the liquid medicament may be provided via a chamber or reservoir that funnels the liquid medicament into the aerosol generator where the liquid medicament is aerosolized for delivery into a user's respiratory system. In other embodiments, a separate container holding the liquid medicament may couple with the aerosolization device to provide the liquid medicament thereto.

In some embodiments, an aerosolization device may include a conduit, an aerosol generator in communication with the conduit, a restrictor plate disposed within the conduit, and an indicator mechanism coupled with the conduit. In many embodiments, some or all of these components are disposed within a housing. In some embodiments, the conduit and/or the aerosol generator may be removably coupled with or received within the housing. By providing a removable conduit and/or aerosol generator, the aerosolization device may be easily cleaned and dried, thus preventing contamination and buildup of pathogens and/or other contaminants.

In some embodiments, the conduit may include a mouthpiece end by which a user may cause an inspiratory flow through the conduit. A user may inhale through the mouthpiece to create the inspiratory flow of air that may transport an aerosolized medicament to the user. In some embodiments, the mouthpiece end of the conduit may deliver the aerosolized medicament to the user at an angle relative to a horizontal plane. Such a delivery angle may be selected based on the dosage and type of medicament to be delivered to the user's respiratory to ensure that a substantial portion of the aerosolized medicament is delivered to the respiratory system without becoming stuck in the user's mouth, throat, and/or other area.

In many embodiments, a sensor is used to determine when a parameter of the inspiratory flow is within a predefined desired or operating range of the aerosolization device and/or the aerosol generator. For example, a flow sensor or pressure transducer may be used to determine a flow rate or pressure differential within the conduit. Other types of sensors and flow parameters may also be employed/measured. For example, the flow parameter can be an inspiratory flow rate, inspiratory pressure, inspiration time, and the like detected by a flow sensor, timer, pressure transducer, or other sensing mechanism. A processing unit coupled with the sensor may compare the sensed value to a stored desired range. In some embodiments, the desired range of a flow parameter for a particular medicament delivery may correspond to the operating range of the aerosol generator. In other embodiments, the desired range of a flow parameter may be narrower or broader than the operating range of the aerosol generator.

In some embodiments, the aerosol generator may include a vibratable mesh. When the parameter of the inspiratory flow is within the desired or operating range, the vibratable mesh may be vibrated for an operating period sufficient to aerosolize substantially all of any liquid medicament disposed on a top of the vibratable mesh. The vibratable mesh may be domed shaped and be vibrated by an annular piezoelectric element (not shown) or other electro-mechanical resonating device that circumscribes the vibratable mesh. The vibratable mesh is vibrated when one or more flow parameters are within an operating range of the aerosol generator. For example, a flow sensor and/or pressure transducer in communication with the conduit may detect that an inspiratory flow rate and/or a pressure differential within the conduit is within an operating range of the aerosol generator. A processor may control a circuit to provide an electric current to the piezoelectric element to vibrate the mesh. Typically, the vibratable mesh will be vibrated at a frequency in the range from about 50 kHz to about 150 kHz to aerosolize the dose of liquid medicament.

In many embodiments, the inhaled air may pass through a restrictor array within the conduit. In one embodiment, the restrictor array may be a restrictor plate that has a plurality of apertures passing therethrough. As air passes through the apertures, the apertures provide an increase in pressure differential that varies according to the inspiratory flow rate within the conduit. The apertures also provide a relatively laminar flow downstream of the restrictor plate compared to upstream of the restrictor plate. In many embodiments, the apertures are disposed along an outer periphery of the restrictor plate. In some embodiments, the vibratable mesh may be located downstream of the restrictor plate or other restrictor array and produce a plume of aerosolized medicament within the relatively laminar flow produced by the restrictor array. In some embodiments, the restrictor array may include multiple restrictor plates in series.

The indicator mechanism may indicate to a user a state of a parameter of the inspiratory flow relative to a predefined desired range. In some embodiments, the indicator mechanism may indicate to the user a state of the aerosolization device in the alternative or in addition to indicating a state of a parameter of the flow. For example, the indicator may be a light, analog/digital display or readout, speaker, vibration-generating device, and/or other feature that alerts a user as to the state of the parameter. In some embodiments, the state of the parameter can be an inspiratory flow rate, inspiratory pressure, inspiration time, and the like detected by a flow sensor, timer, pressure transducer, or other sensing mechanism. The indictor may inform the user if they are within or outside of the desired range for the parameter.

In some embodiments, an 'end of dose' indication can be provided to a user when an entire dose of the medicament has been aerosolized. Such an indication may be provided upon a sensor, such as a load or flow sensor, detects that substantially all of the medicament has been aerosolized. Another indication may also be provided to the user informing them of when the liquid medicament is actually being aerosolized by the activated vibratable mesh. Such indications of a state of the flow parameter and/or state of the aerosolization device can be provided by the indicator mechanism described above, such as by providing a distinguishable indication from the indication of the state of the flow parameter. For example, the state of the flow parameter may be indicated by a green light and the indication of the end of dose may be provided by a blue light. In other embodiments, the end of dose indication and/or the aerosolization indication may be provided by one or more separate indicator mechanisms.

In some embodiments, the indicator mechanism may be used direct a user in how to properly inhale and thereby ensure proper delivery of the medicament to the user's respiratory system. To do so, the indicator mechanism may alert the user when a parameter, such as an inspiratory flow rate within the conduit, is within a predefined desired range. The aerosol generator may be configured to aerosolize the liquid medicament when the inspiratory flow is within the redefined flow rate range. For example, the predefined desired range of the inspiratory flow rate within the conduit may be between about 5 and 14 liters per minute (L/min). An indication as described above, such as a light or sound emitted by a speaker, may be produced to alert the user that the user's inhalation is maintaining the inspiratory flow rate within the desired range, and thus when the aerosol generator is active.

In some embodiments, a first indication may be provided with the parameter is within the desired range and a second indication may be provided when the parameter is outside of the desired range. For example, the first indication may include a light being turned on or a sound, such as a beep, being emitted. The second indication may include a light being turned off or a previous continuously emitted sound ceasing. Other indications may include emitting a different color of light or different frequency of sound than the first indication to indicate a change in state of a parameter. In some embodiments, the second indication can alert a user whether the state of the parameter is higher or lower than the desired range. For example, a flashing light may be emitted with a relatively long period between flashes to alert the user when the state of the parameter is lower than the desired range and a flashing light having a relatively short period between flashes may be emitted to alert the user that the state of the parameter is higher than the desired range. Similar uses of vibrations and sounds may be used in conjunction with, or in alternative to, light indicators.

In some embodiments indicating to the user the state of the parameter of the inspiratory flow relative to the predefined desired range may include the indicator mechanism providing a first indication when the parameter of the inspiratory flow is within the predefined desired range, the indicator mechanism providing a second indication when the parameter of the inspiratory flow is within a predefined secondary range (i.e., potentially an acceptable, but less than optimum, range), and the indicator mechanism providing a third indication when the parameter of the inspiratory flow is outside of both the predefined desired range and the predefined secondary range.

In some embodiments, the aerosolization device may further include an input device for receiving and setting the predefined desired range of the parameter of the inspiratory flow. For example, the input device may include a barcode scanner, radio frequency identification (RFID) reader, keyboard, or any other input device that can receive an input from the user regarding one or more parameters of the inspiratory flow, such as a desired flow rate, inspiratory pressure, or inspiration time. In some embodiments, the desired flow rate may be visually or otherwise encoded on the medicament delivery container, and read by the aerosolization device therefrom.

In some embodiments, the parameter of the inspiratory flow may include the inspiratory flow rate within the conduit. The predefined desired range of the inspiratory flow rate may be between about 5 and 14 liters per minute (L/min). In some embodiments, the parameter of the inspiratory flow may include the inspiration time. The predefined desired range of the inspiration time may be between about 5 and 26 seconds. In some embodiments, multiple parameters may be measured and referred to. For example, in one embodiment, a certain amount of inspiration time of a minimum inspiratory flow may be necessary.

In some embodiments, the aerosolization system may include electronic elements including, but not limited to, a processing element and a memory unit. The processing element may be used to control the actuation of the aerosol generator, indicator mechanisms, and input devices, as well as any sensors such as flow sensors and pressure transducers. The memory unit may be configured to store settings and ranges set by the input device for the parameters of the indicator mechanism and/or aerosol generator. The memory unit may also be configured to store data related to past aerosolization sessions, as well as information provided by medicament delivery vessels attached thereto.

Figure 1B:
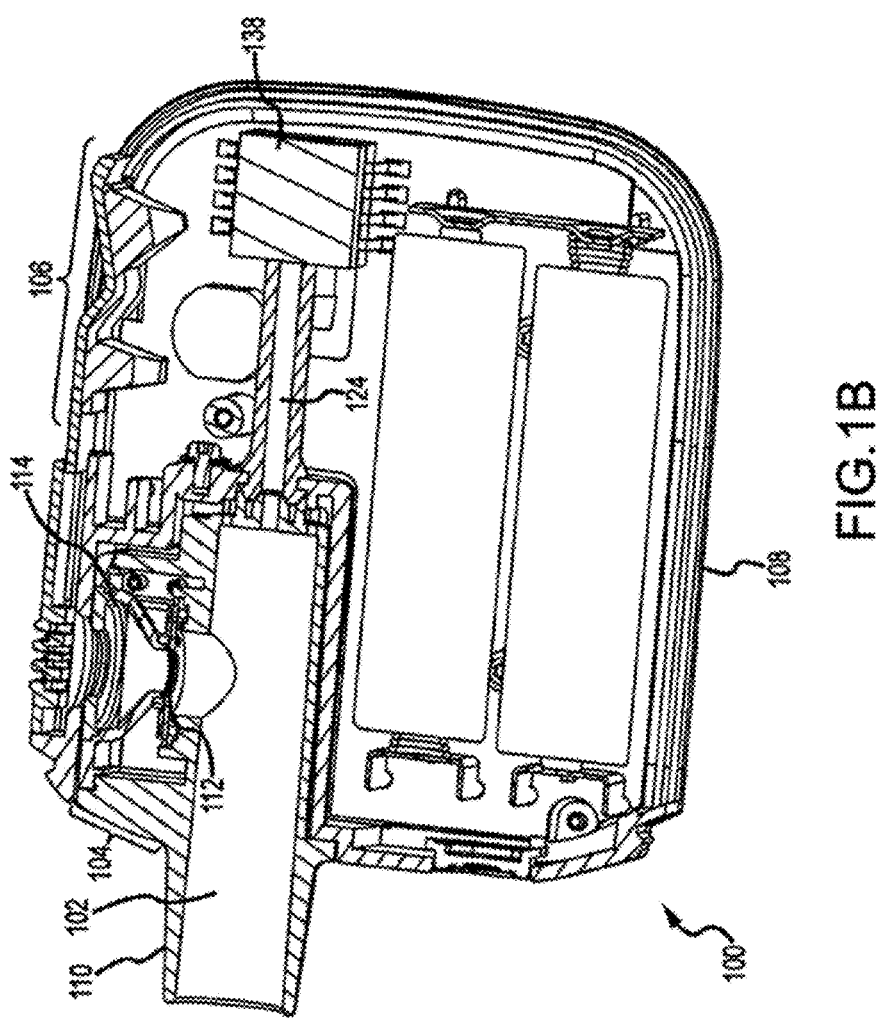
FIG. 1B shows a cross section of FIG. 1A according to embodiments of the invention.

Turning now to the drawings, FIGS. 1A and 1B illustrate an aerosolization device 100, in accordance with various embodiments of the invention. Aerosolization device 100 includes a conduit 102 and an aerosol generator 104 in communication with the conduit 102. The aerosolization device 100 may also include one or more indicator mechanisms 106, shown here as indicator lights. The one or more indicator mechanisms may be coupled with the a housing 108, or some other portion of device 100. Conduit 102 and aerosol generator 104 may also optionally be coupled with housing 108.

In some embodiments, conduit 102 may include a mouthpiece end 110 through which a user may inhale to produce an inspiratory flow to deliver aerosolized medicament to the user's respiratory system. As seen in FIG. 1B, the aerosol generator 104 may include a vibratable mesh 112. Liquid medicament can be dispensed onto the vibratable mesh 112, either directly from a vial of liquid medicament or indirectly by being funneled onto the vibratable mesh 112 by tapered walls of a fluid receiving chamber 114. In many embodiments, the vibratable mesh 112 is vibrated via a mechanism controlled by a processor to aerosolize a volume of liquid medicament when a flow rate of the inspiratory flow is within an operating range of the aerosol generator 104. When vibrated, the vibratable mesh 112 operates to produce a plume of aerosolized medicament within the conduit 102 such that the aerosolized conduit can be inhaled into the user's lungs.

Exemplary aerosol generators that can be used are also described in U.S. Pat. Nos. 5,164,740; 6,629,646; 6,926,208; 7,108,197; 5,938,117; 6,540,153; 6,540,154; 7,040,549; 6,921,020; 7,083,112; 7,628,339; 5,586,550; 5,758,637; 6,085,740; 6,467,476; 6,640,804; 7,174,888; 6,014,970; 6,205,999; 6,755,189; 6,427,682; 6,814,071; 7,066,398; 6,978,941; 7,100,600; 7,032,590; 7,195,011, incorporated herein by reference. These references describe exemplary aerosol generators, ways to manufacture such aerosol generators and ways to supply liquid to aerosol generators, and are incorporated by reference for at least these features.

In some embodiments, the one or more indicator mechanisms 106 may include lights, such as LEDs. Indicator mechanisms 106 may also include speakers/or and vibration generating mechanisms to direct users as to a state of the aerosolization device. For example, indicator mechanisms 106 can be used to direct a user when the aerosolization device 100 is ready for use. Indicator mechanisms 106 may also indicate a state of a parameter of the inspiratory flow created by the user. For example, the indicator mechanisms 106 may instruct a user to alter an inhalation rate to increase or decrease a flow rate within the conduit 102 to ensure proper delivery of the aerosolized medicament and/or to ensure that the flow rate is within the operating range of the aerosol generator 104 such that the vibratable mesh 112 aerosolizes the liquid medicament. Indicator mechanisms 106 may also be used to indicate to a user when substantially all of a dose of liquid medicament has been aerosolized and/or inhaled. Additional sensors may be required in order to provide the functionality described above.

In some embodiments, the aerosolization device 100 include a processing unit or integrated circuit (IC) 138 that controls the function of or runs computer code to control other electronic components of the aerosolization device 100. Aerosolization device 100, including IC 138, may be powered by batteries 140 that are coupled with IC 138. IC 138 may be electrically coupled with electronic components, such as any sensors, indicating mechanisms 106 and/or a piezoelectric element of aerosol generator 104. IC 138 can control the actuation of the indicator mechanisms and/or the aerosol generator 104 based on information received from any sensors, such as flow sensors or pressure transducers in fluid communication with the conduit 102. In some embodiments, IC 138 may be electrically coupled with the conduit 102 and/or the aerosol generator 104 using a plug 124. The conduit 102 and/or aerosol generator 104 may be removable from housing 108. The conduit 102 and/or aerosol generator 104 may be inserted into housing 108 and interfaced with plug 124 to supply power to and control actuation of the aerosol generator 104 based on measurements from sensors in fluid communication with conduit 102. For example plug 124 may have a male connector 144 that interfaces with a female connector 146 on conduit 102. In some embodiments, plug 124 may include a female connector that interfaces with a male connector on conduit 102.

Figure 2:
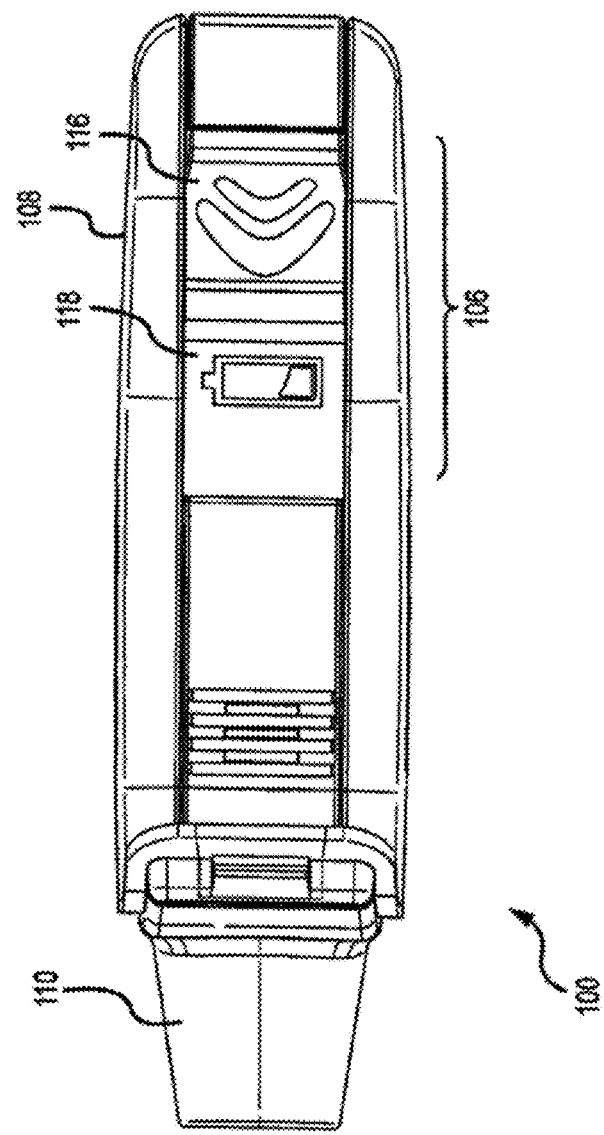
FIG. 2 depicts a front of the aerosolization device of FIG. 1A according to embodiments of the invention.

FIG. 2 shows a top view of aerosolization device 100 and indicator mechanisms 106 according to embodiments of the invention. In some embodiments, indicator mechanisms 106 can include a breathing indicator 116 and a battery indicator 118. Breathing indicator 116 can direct a user when and how to breath to maximize delivery of the aerosolized medicament to the user's lungs. In some embodiments, breathing indicator 116 can include multiple indicators, such as various colored LEDs, to provide the user more detailed guidance. Breathing indicator 116 may be in the shape of a chevron that includes 3 colors of LEDs.

In some embodiments, optimal pulmonary delivery of medicaments such as liquid insulin occurs at specified flow rates and inspiratory times. For example, an optimal flow rate may be between about 5 and 14 L/min, or more often between about 7 and 14 L/min. Flow rates that are too high or too low can result in losses in the amount of aerosolized medicament delivered to the proper locations of a user's respiratory system, for example by lack of entrainment of the medicament in the airflow of the inhaler or by impaction of the medicament in parts of the respiratory system where deposition is not desired. The optimal flow rate may depend on the diameter of the airflow channel in the inhaler. An optimal inspiratory time may be between 6 and 24 seconds. Breathing indicator 116 can be used to direct a user to maintain an inhalation within these parameters.

In one embodiment, a light, such as a steady green light emitted from an LED, will be produced using breathing indicator 116 to instruct a user that flow within the aerosolization device 100 is within the operating range of the aerosolization device 100 to aerosolize a dose of medicament. As a user inhales at the mouthpiece end 110 of the conduit 102, the inhalation flow rate is detected by a flow sensor or a pressure transducer that can convert a pressure differential within the conduit 102 into a flow rate. The detection of an inhalation having proper flow parameters results in activation of the aerosol generator 104 to produce aerosolized medicament particles into the conduit 102. The light from breathing indicator 116 may be slowly flashed to indicate that the user is breathing too slowly (i.e., causing a low flow rate) as compared to the operating range, should aspiratory conditions change. For example, a flashing green light may be emitted having a period of between about 500 and 1000 milliseconds (ms) and a frequency of about 1.25 hertz (Hz) to indicate that the aerosolization device 100 is activated during a time with little or no air flow, such as before the user begins to inhale through the mouthpiece 110. The light may be flashed quickly to direct the user that they are breathing too quickly (i.e., causing a high flow rate). For example, a flashing green light may be emitted from the breathing indicator 116 having a period of between about 50 and 250 ms and a frequency of about 6.25 Hz when the flow rate is excessive. The aerosol generator 104 may be configured to not aerosolize any medicament when the flow rate is too high or too low.

The breathing indicator 116 may produce a different colored light as an "end of dose" indictor to indicate that substantially all of the dose of medicament has been delivered. For example, a blue light may be emitted for a period of time, such as between about 1 and 10 seconds to alert the user that substantially all of the dose has been aerosolized and inhaled. Delivery of the 'entire' dose may be predefined as when at least about 95% of the dose is delivered, more preferably 98% and most preferably when more than 99% of the dose is aerosolized. To receive the dose, the user may take several inhalations or a single inhalation depending on the volume of liquid drug to be delivered and the user's breathing capacity. Each inhalation may be monitored by the device, with feedback provided to the user via indicator 116, to insure proper delivery to the lungs. In some embodiments, the operation of the end of dose indicator may be delayed for a period, such as up to about 5 seconds after substantially all of the dose has been delivered, thus providing a "chaser" of air into the lungs. This chaser may serve to clear the upper airway and maximize the amount of the dose that is transported to the user's lungs. In other embodiments, the operation of the end of does indicator may be delayed until the user completes the inhalation during which the end of does was detected. In some embodiments, the inhaler is automatically shut off after the end of the dose is reached, for example shortly after the end of dose indication is given to the user.

In embodiments where the conduit 102 and/or aerosol generator 104 are removable from housing 108, a light may be emitted to instruct a user that one or both of the conduit 102 and the aerosol generator are not completely seated, coupled together, and/or engaged within the housing 108. It will also be appreciated that other shapes and numbers of lights may be used in breathing indicator 116. Breathing indicator 116 may also use different numbers or types of lighting elements, colors of light, intensities of light, flashes of light having different periods, vibration patterns, sounds, and/or any combination of such indications to direct a user on how to properly inhale using the aerosolization device 100. For example, breathing indicator 116 may include a multi color LED, which may provide any or all of the indications made by breathing indicator 116. A multi color LED has the capability to generate light of different colors from within the same LED package, depending on how it is electrically driven. For example, the same LED package may produce green light at one time, and blue light at another time. A multi color LED can be flashed in the same way that a single color LED can be flashed. In some embodiments, a single multi color LED provides an indication that the user is breathing too slowly, an indication that the user is breathing at a desired flow rate, an indication that the user is breathing too quickly, and an end of dose indication, of the types described above, or of different types. Indicator mechanisms 106 may also be used to provide other indications related to the aerosolization device 100.

In some embodiments, the battery indicator 118 can indicate to a user an amount of charge remaining on a battery of the aerosolization device 100 which powers the functions thereof. The battery indicator may be a digital readout of a charge level or may be a light emitting device, such as an LED, that emits one or more colors of light to indicate a relative state of charge. For example, the battery indicator 118 may emit a single color light to indicate when a charge is low. In other embodiments, the battery indicator 118 may emit three or more colors of light to indicate various levels of charge to show a status of the charge over time.

Figure 2A:
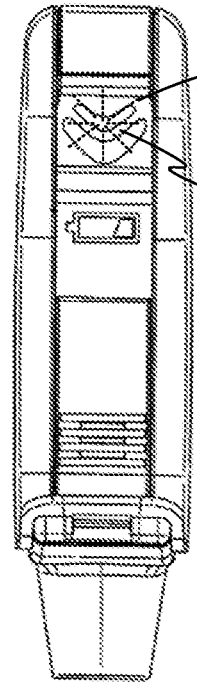
FIGS. 2A-2D illustrate four different indications of states in the operation of the aerosolization device of FIG. 1A, in accordance with embodiments of the invention.
Figure 2B:
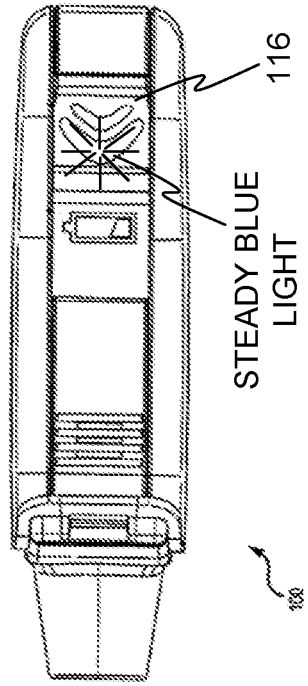
Figure 2C:
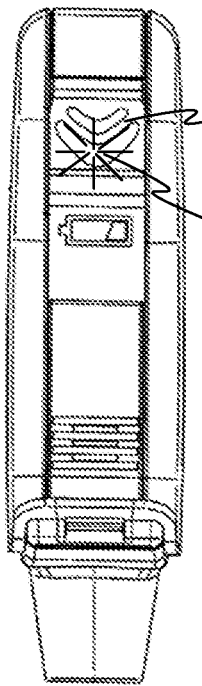
Figure 2D:
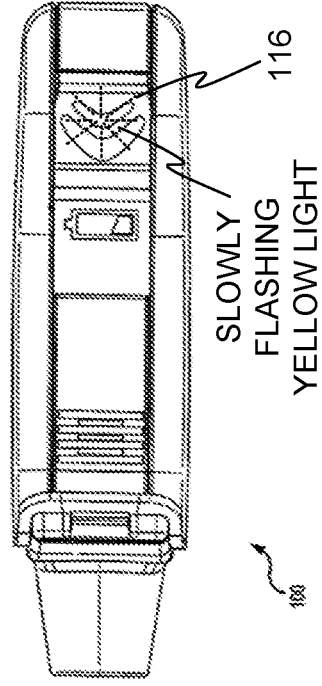

FIGS. 2A-2D illustrate four different indications of states in the operation of aerosolization device 100, in accordance with one embodiment. FIG. 2A shows a first indication in the form of a steady green light, as may be used to indicate that the flowrate is in a desired range between a first threshold value and a second threshold value. FIG. 2B shows a second indication in the form of a rapidly flashing yellow light, as may be used to indicate that the flowrate is above the desired range. FIG. 2C shows a third indication in the form of a slowly flashing yellow light, as may be used to indicate that the flowrate is below the desired range. FIG. 2D shows a fourth indication in the form of a steady blue light, as may be used to indicate that dosage is complete.

FIGS. 3A-3K depict embodiments of flow restrictor plates that may be positioned within a conduit, such as conduit 102 of FIGS. 1A and 1B. Restrictor plates, such as restrictor plate 300a, create resistance to and limit airflow through a conduit while adding minimal to no length to a conduit.

The restrictor plate 300a provides an increase in pressure differential that varies with inspiratory flow rates. This pressure differential exists between the conduit and outside of the conduit and/or atmospheric pressure such that as the user's inhalation force increases, the pressure differential drops to maintain a relatively constant flow rate within the conduit that stays in a desired flow rate range. In some embodiments, the pressure differential increases in a linear relationship with the flow rate as the user's inhalation force increases. Sensory feedback provided by sensors and/or indicator mechanisms, such as those described above, may allow the user to relate inspiratory pressure with the required flow rate required to operate the aerosol generator. Restrictor plate 300a defines a plurality of apertures 302a for air to pass through. Apertures 302a can be positioned around an outer periphery of the restrictor plate 300a such that air passing through the apertures forms a relatively laminar flow downstream of the restrictor plate 300a. Apertures 302a can be of any shape or size to create a relatively laminar flow. For example, apertures may be circular and have diameters ranging between about 0.5 mm to 1.5 mm. The size and pattern of the plurality of apertures 302a can prevent airflow through a solid center portion of the restrictor plate 300a, while allowing airflow through the apertures on the periphery thereof.

Figure 3A:
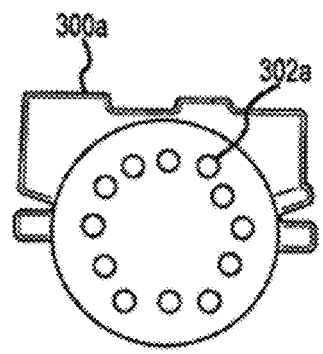
FIGS. 3A-3K illustrate restrictor plates according to embodiments of the invention.
Figure 3B:
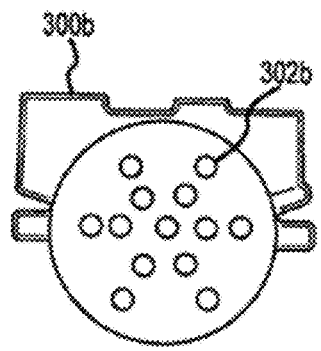
Figure 3C:
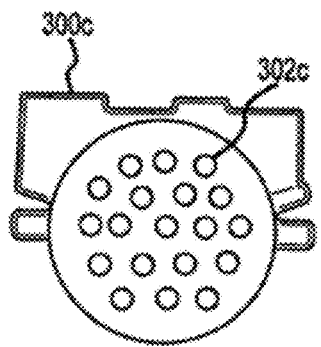
Figure 3D:
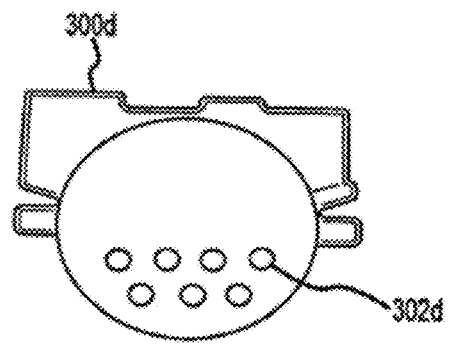
Figure 3E:
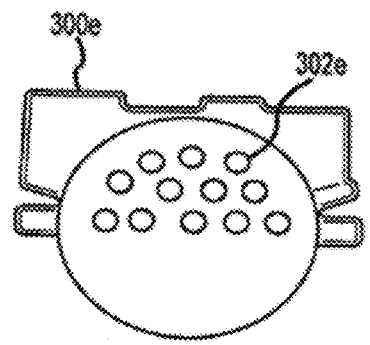
Figure 3F:
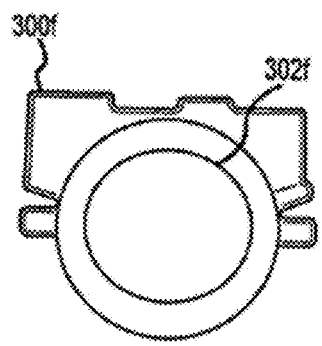
Figure 3G:
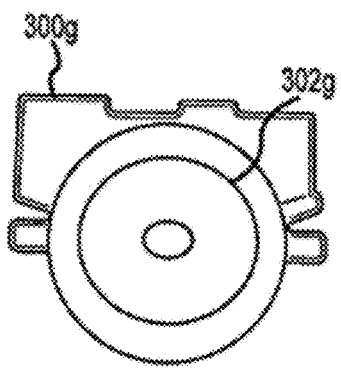
Figure 3H:
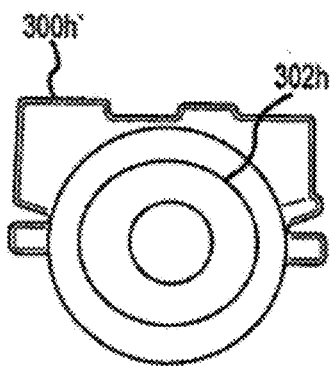
Figure 3I:
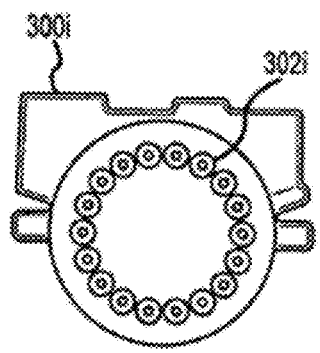
Figure 3J:
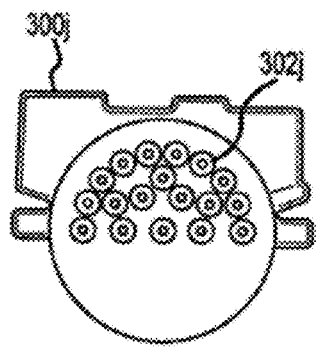
Figure 3K:
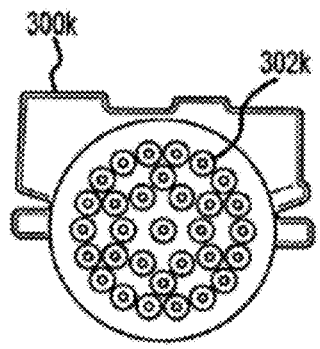

FIGS. 3B-3K show embodiments of restrictor plates defining alternative arrangements of apertures. For example, FIG. 3B shows restrictor plate 300b defining a plurality of apertures 302b arranged in a spoke pattern. FIG. 3C shows a restrictor plate 300c defining a plurality of apertures 302c arranged in a circular pattern. FIG. 3D shows a restrictor plate 300d defining a plurality of apertures 302d arranged in a half circle pattern along a bottom of the restrictor plate 300d. FIG. 3E shows a restrictor plate 300e defining a plurality of apertures 302e arranged in a half circle pattern along a top of the restrictor plate 300e. FIG. 3F shows a restrictor plate 300f defining an aperture 302f that reduces an effective diameter of a conduit. FIG. 3G shows a restrictor plate 300g defining an aperture 302g that reduces an effective diameter of a conduit. FIG. 3H shows a restrictor plate 300h defining an aperture 302h that reduces an effective diameter of a conduit. FIG. 3I shows a restrictor plate 300i defining a tightly grouped plurality of apertures 302i arranged along an outer periphery of the restrictor plate 300i. FIG. 3J shows a restrictor plate 300j defining a plurality of apertures 302j arranged in a half circle pattern along a top half of the restrictor plate 300j. FIG. 3K shows a restrictor plate 300k defining a plurality of apertures 302k arranged in a circular pattern.

Figure 4:
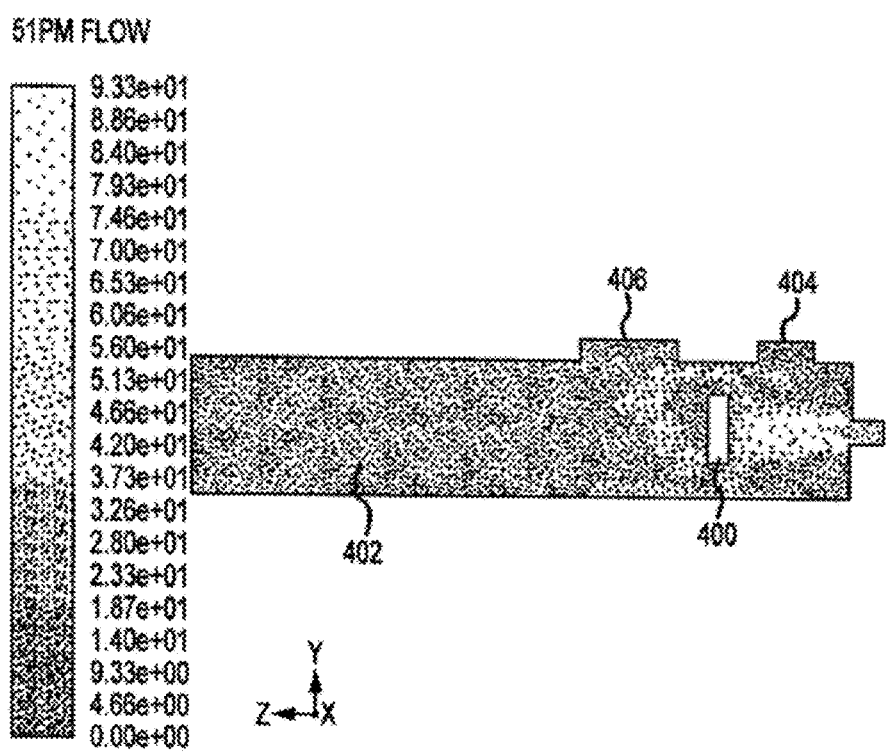
FIG. 4 shows a restrictor plate within a conduit of an aerosolization device according to embodiments of the invention.

FIG. 4 illustrates a restrictor plate 400 positioned within a conduit 402 in accordance with embodiments of the invention. Restrictor plate 400 is disposed within the conduit between a pressure transducer 404 that is in fluid communication with an interior of the conduit and an aerosol generator 406. The pressure transducer 404 monitors a pressure differential within the conduit 402 relative to outside of the conduit and/or atmospheric pressure. A processing unit or IC, such as IC 138 of FIGS. 1A and 1B, may execute software that converts the pressure reading to a flow rate throughout the conduit 402. This flow rate may be used to determine when to activate the aerosol generator 406 to aerosolize a volume of liquid medicament. Restrictor plate 400 may have the characteristics of the restrictor plates 300a-300k discussed above. Restrictor plate 400 creates a laminar flow upstream of the aerosol generator 406 such that the aerosolized medicament is deposited within the laminar flow and entrained within the laminar flow before the aerosolized medicament contacts a wall of the conduit 402 opposite of the aerosol generator 406, in order to maximize the amount of medicament delivered to the user.

Figure 5:
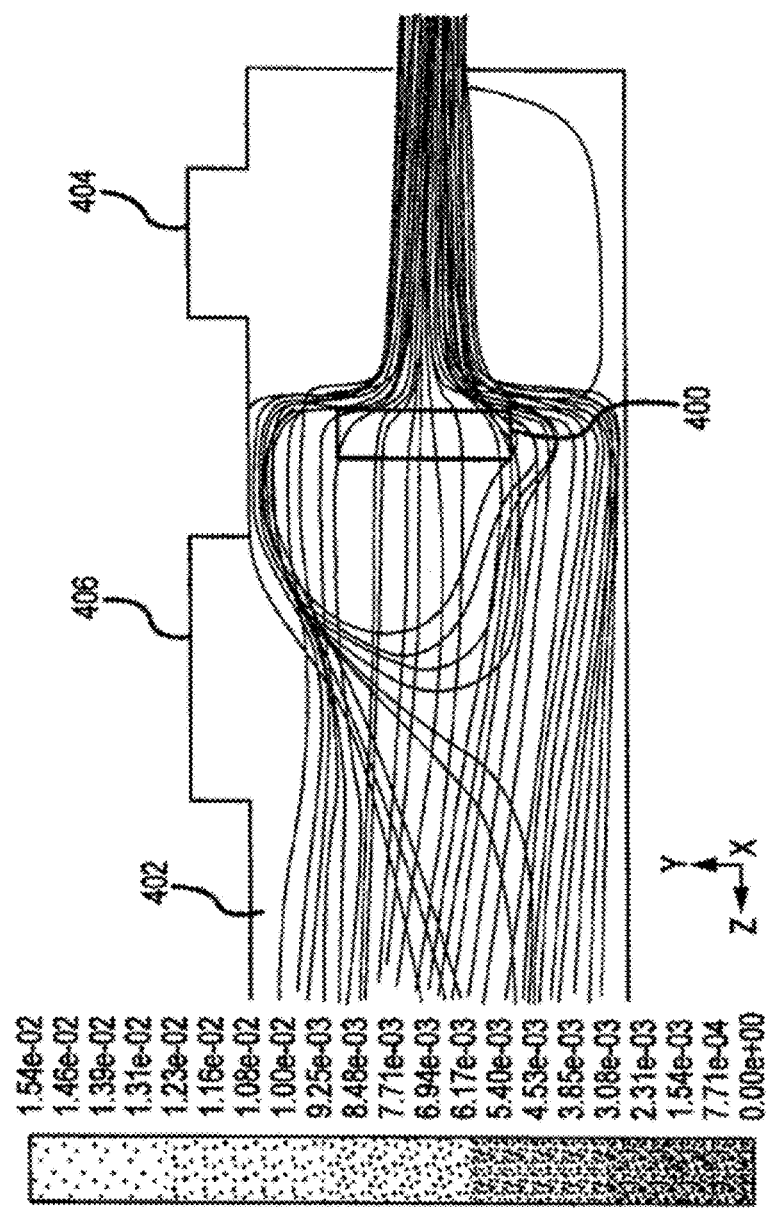
FIGS. 5-7 show laminar flows created by restrictor plates within the conduit of FIG. 4 according to embodiments of the invention.
Figure 6:
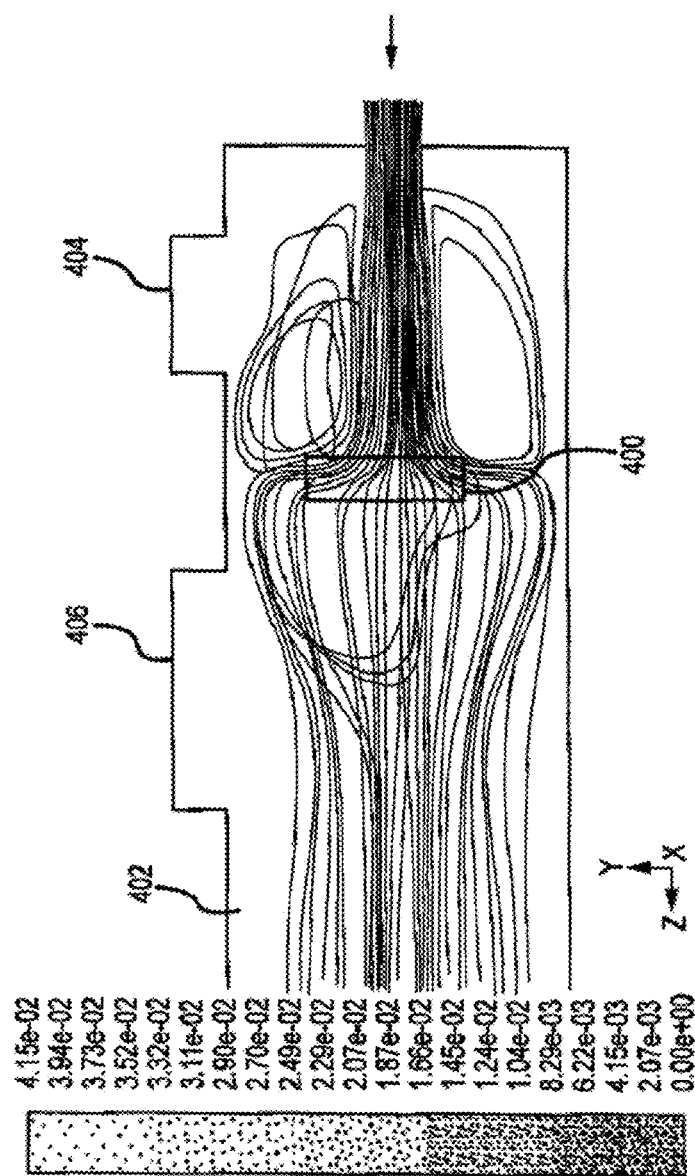
Figure 7:
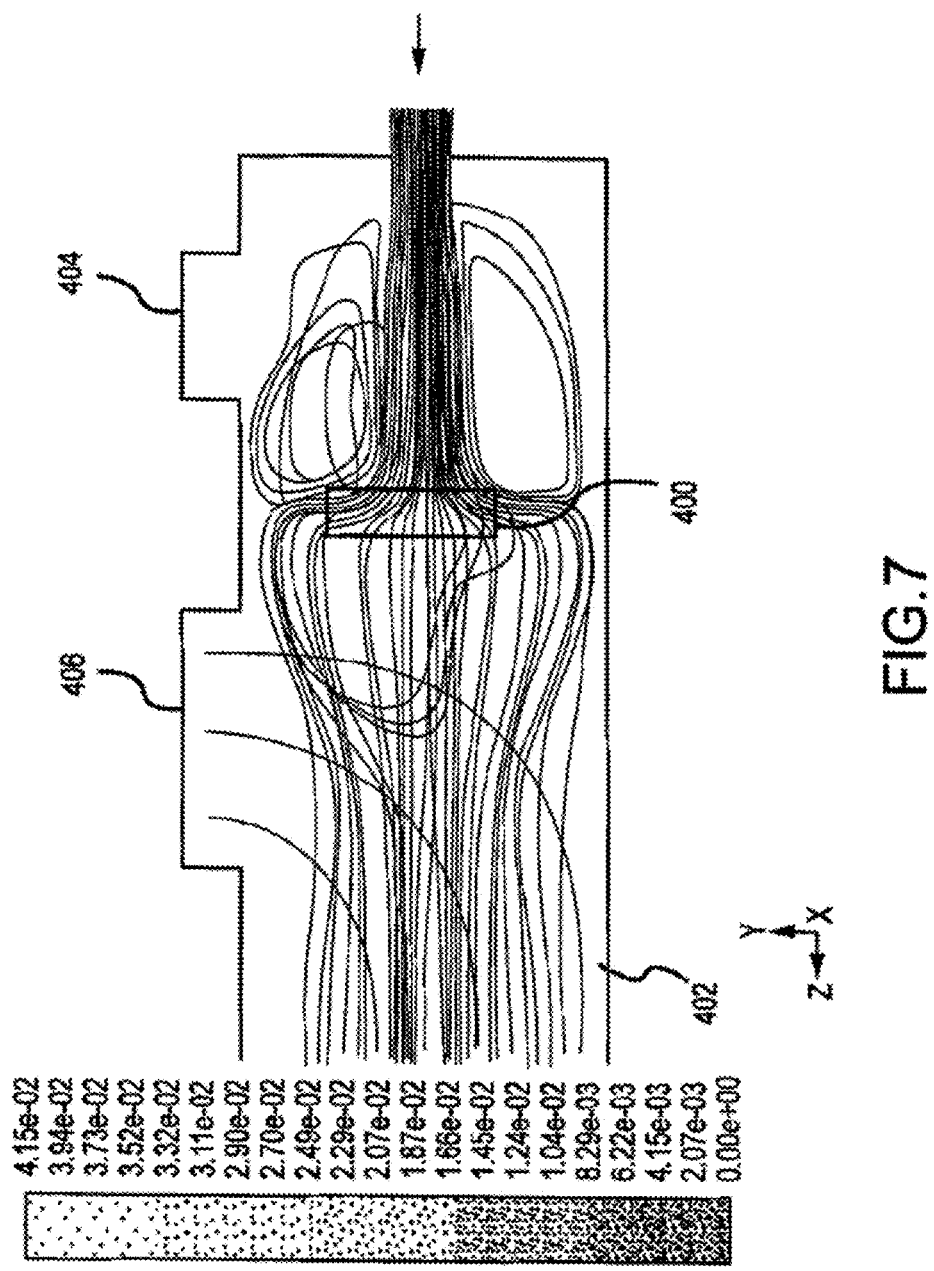

FIGS. 5-7 are laminar flow diagrams of airflow through conduit 402 and restrictor plate 400 having a structure similar to restrictor plate 300a. As airflow reaches restrictor plate 400, the pressure differential is increased and a relatively laminar flow is created to contact aerosolized medicament. The laminar flow provides a consistent velocity field to deliver the aerosolized particles to the user's respiratory system in a consistent manner while minimizing impactive losses. Additionally, the laminar flow minimizes an amount of aerosolized medicament that may be deposited on a wall of the conduit. FIG. 7 shows the laminar flow contacting aerosolized medicament produced by the aerosol generator 406. The aerosolized medicament is entrained in the laminar flow before the medicament contacts a wall opposite of the aerosol generator 406. The entrained aerosolized medicament is then carried out of the conduit 402 to a user's respiratory system.

Figure 8A:
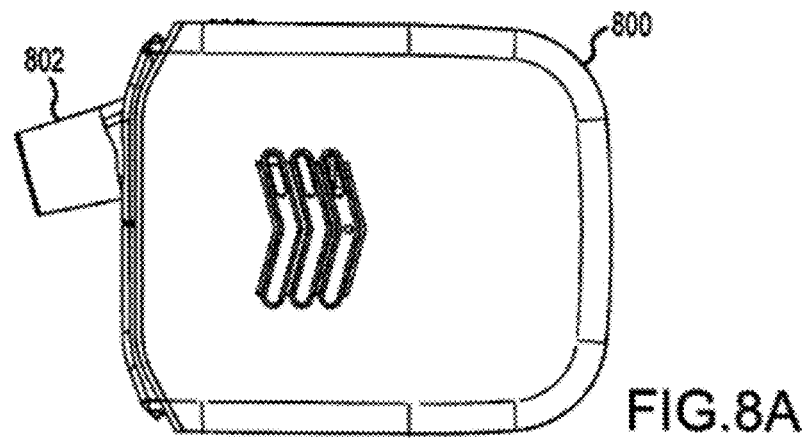
FIGS. 8A-8C depict conduits having mouthpiece ends at various angles according to embodiments of the invention.
Figure 8B:
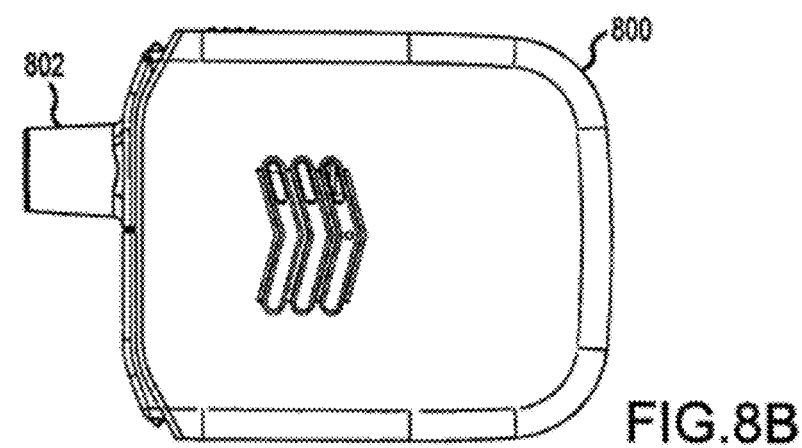
Figure 8C:
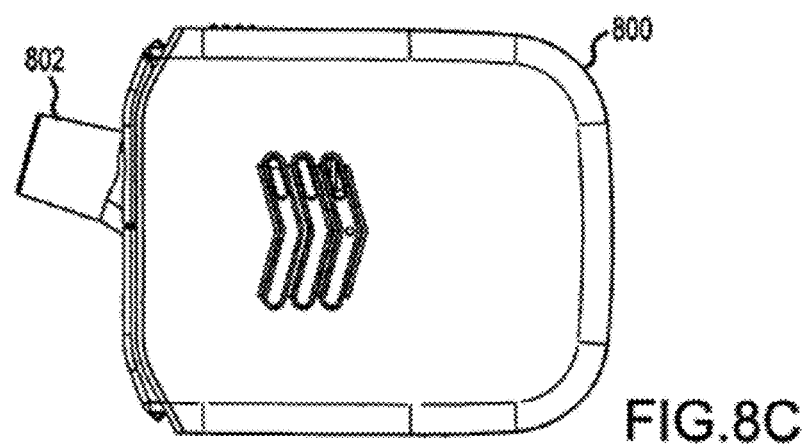

FIGS. 8A-8C show an aerosolization device having a mouthpiece end angled at various angles to direct airflow into a user's respiratory system. Mouthpiece end angles may be set based on the volume of a dose, type of medicament to be delivered, and length and diameter of the conduit of an aerosolization device. FIG. 8A shows an aerosolization device 800 having a mouthpiece end 802 angled downward 15° relative to a horizontal plane. FIG. 8B shows aerosolization device 800 having mouthpiece end 802 parallel relative to a horizontal plane. FIG. 8C shows aerosolization device 800 having mouthpiece end 802 angled upward 15° relative to a horizontal plane. Other angles relative to a horizontal plane of up to 30° up or down relative to a horizontal plane may be used to maximize delivery of the medicament to the user's respiratory system.

Figure 9:
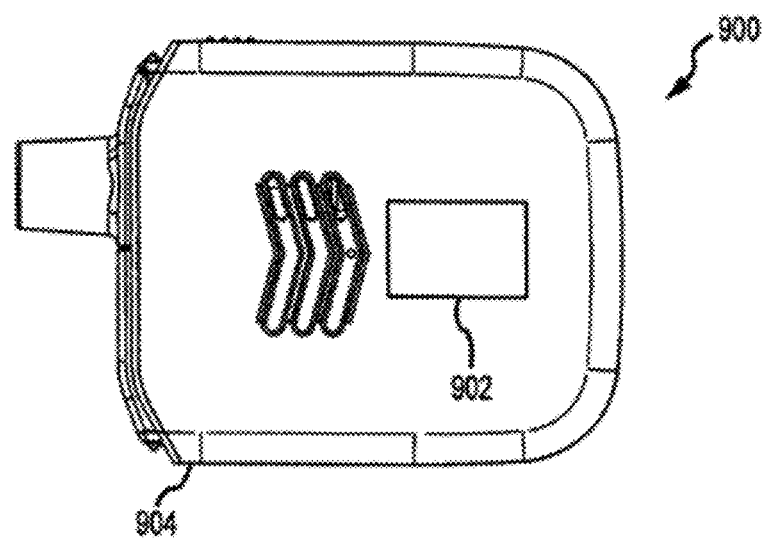
FIG. 9 shows an input device on an aerosolization device according to embodiments of the invention.

FIG. 9 shows an aerosolization device 900 having an input device 902 coupled with a housing 904. In some embodiments, input device 902 may be coupled with a conduit. Input device 902 is configured to receive an input from a user that sets parameters for an inspiratory flow determined by a pressure transducer (not shown) within the conduit. The input may be manually entered by a user, provided via wireless interface, provided via wired interface, such as universal serial bus (USB), or in any other manner. The parameters, which may include a flow rate, an inspiratory pressure, an inspiratory time, and the like, may be used to determine when an aerosol generator of the aerosolization device 900 are actuated, as well as to set ranges for indicator mechanisms (not shown) that direct the user on when and how to breath. An input device 902 may include a keyboard or similar interface, a barcode scanner or RFID reader to receive flow parameters from a user or a container or label of the medicament. Aerosolization device 800 may be configured similar to any of the aerosolization devices described herein, and may include the same or similar features.

Figure 10:
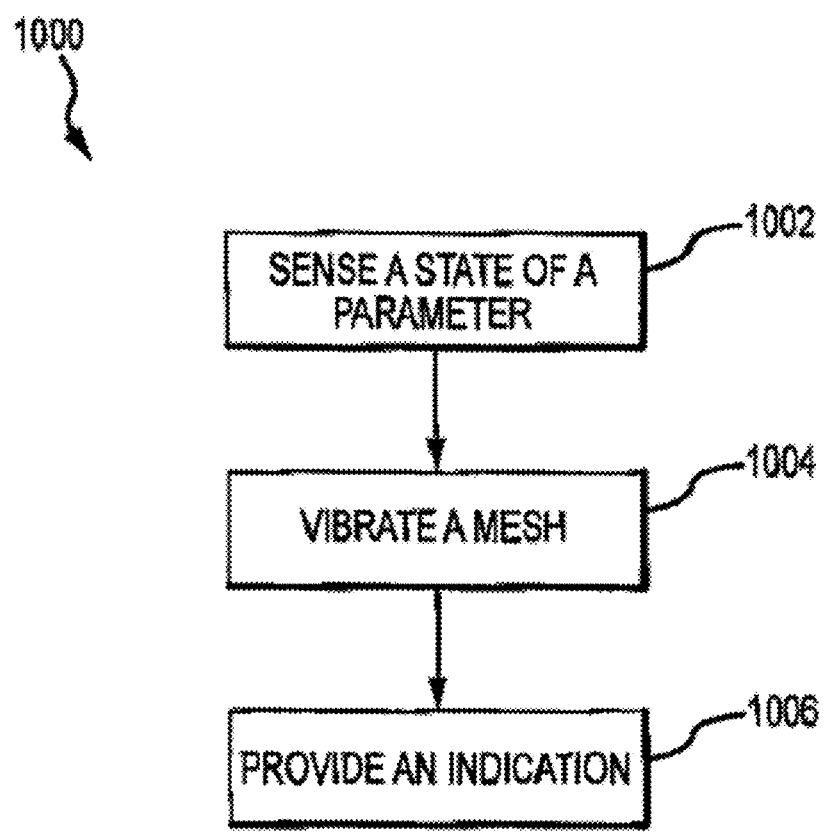
FIG. 10 is a block diagram of a method of using an aerosolization device according to embodiments of the invention.

FIG. 10 depicts a method 1000 of delivering an aerosolized medication to a user's respiratory system using the aerosolization devices described herein. The method may include sensing a state of a flow parameter of an inspiratory flow within a conduit at block 1002. Sensing a state of a flow parameter may be done using sensors, such as a flow sensor or the pressure transducer 404 of FIG. 4. The method may also include vibrating a mesh of an aerosol generator in communication with the conduit to aerosolize a volume of a liquid medicament at block 1004. This vibration produces a plume of aerosolized medicament within a conduit of the aerosolization device when a state of the flow parameter is within a predefined desired range. For example, when an inspiratory flow rate determined by the pressure transducer is within an operating range of the aerosolization device, the mesh may be vibrated. The plume of aerosolized medicament may be provided within a relatively laminar flow produced by a restrictor plate disposed within the conduit upstream of the plume of aerosolized medicament. The laminar flow sweeps the aerosolized medicament toward a mouthpiece end of the conduit before the medicament contacts a wall of the conduit opposite the aerosol generator. The aerosolized medicament is then directed into a user's respiratory system. The method may further include providing an indication using an indicator mechanism coupled with the conduit of the state of the flow parameter relative to the predefined desired range at block 1006.

In some embodiments, providing an indication may include providing a first indication when the flow parameter is within the predefined desired range and providing a second indication when the flow parameter is outside of the predefined desired range. In other embodiments, providing an indication may include providing a first indication when the flow parameter is within the predefined desired range, providing a second indication when the flow parameter is within a predefined secondary range, and providing a third indication when the flow parameter is outside both the predefined desired range and the predefined secondary range.

By indicating the state of the flow parameter within intermediate ranges, a user can alter a rate of inhalation to maximize the efficiency of a delivery of aerosolized medicament. For example, for an aerosol generator having an operating range for a flow rate of between about 5 and 14 L/min, a predefined desired range may be from between about 8 and 11 L/min. A predefined secondary range may be set within the remaining operating range of the aerosol generator. For example, the secondary range may be between about 5 and 7 L/min and between about 12 and 14 L/min. A first indication, such as a green light, may be provided when the flow rate is within the predefined desired range. A second indication, such as a yellow light, may be provided when the flow rate is outside of the desired range but within the secondary range. In other embodiments, a slowly flashing yellow light may be used to indicate that the flow rate is within the lower secondary range and a quickly flashing yellow light can indicate that the flow rate is within the higher secondary range. A third indication, such as a red light, may be used to indicate that flow rate is outside of both the desired range and the secondary range.

Such systems that provide intermediate ranges can help a user correct or otherwise adjust an inhalation rate to maintain a flow rate within a desired or operating range of the aerosolization device before the flow rate is unacceptably inefficient or inoperable to actuate the aerosol generator. This can help a user develop more consistent and efficient inhalations. Multiple intermediate ranges, both within and outside of, the operating range of the aerosol generator may be provided to further aid a user in adjusting the inhalation rate. Additionally, the intermediate ranges may be focused on ensuring that an efficient flow rate range is maintained, rather than ensuring that an operating range of the aerosol generator is maintained.

In some embodiments, the method may further include providing an indication that the liquid medicament is ready to be aerosolized and providing an indication that substantially all of the liquid medicament has been aerosolized. The method may optionally include receiving an input via an input device of the aerosolization device to set the predefined desired range of the flow parameter.

Experimental Results

A series of in silico, in vitro, and human user studies were conducted to determine the preferred operating conditions for an inhaler as described above. It was desired to provide relatively large quantities of inhaled medicament (up to 255 ul, e.g.) to a patient with minimal loss of medicament in the inhaler, to provide the dose relatively quickly (within 1-5 breaths, e.g.), and to preferentially deposit the medicament in the peripheral portion of the user's lungs rather than the central portion of the user's chest.

The studies were based on a vibrating mesh aerosol generating technology developed by Aerogen, Inc., of Galway, Ireland, and used in Aerogen's Solo nebulizer. The mesh includes over 1000 funnel shaped apertures, and can produce respirable particles in the 3.5-5 micron diameter range at an output rate of 0.4-0.6 mL/min.

The in silico studies suggested that when using a flow path diameter of 10 mm and introducing the aerosol into the flow path from the side, an air flow rate of 5 L/min or more would entrain aerosol with minimal contact on the opposing wall of the flow path.

The in vitro studies varied the particle size, aerosol output rate, plume force, and inspiratory flow rate, with the intention of identifying the highest percent of dose delivered distal to the trachea of a model throat. A number of orifice arrays such as those described above were tested, acting as a fixed resistor to produce sufficient back pressure without creating turbulence of the inhaled gas. The orifice patterns shown in FIGS. 3E and 3I were included in the tests, with the pattern of FIG. 3I being somewhat preferred. The in vitro studies suggested an optimum flow rate of 7 to 14 L/min for the particle size tested. This range of flow rates is sufficient to entrain the aerosol in the flow path, but is relatively low in comparison with prior devices, contributing to good deposition in the peripheral portion of the lungs.

Several users were also tested to evaluate whether the various signals provided by the device could assist in leading the users to breath properly to ensure optimal medicament deposition. A simulator was used for these tests. Naïve subjects were trained to interpret the meaning of the light signals emitted by the inhaler, and were requested to adjust their breathing to maintain a desired flow rate (for example indicated by a steady green light). In a test of nine adult subjects, all of the subjects learned by their third inhalation to maintain an inspiratory flow rate of 7-14 L/min, and all were able to hold their breaths for five seconds after an inhalation. Six of the nine subjects also attempted to maintain an inspiratory flow rate of 9-12 L/min, but were less likely to complete an inspiration without exceeding these limits. The subjects also reported being less subjectively comfortable with the narrower range.

In addition, a human study was done to evaluate the actual effectiveness of the inhaler and its operation in delivering medicament to the peripheral lung tissue. For this study, the results were measured using 2-D planar scintigraphy. This was a randomized crossover study on six healthy adults between 18-60 years of age with no history of smoking or lung disease. All subjects were randomized to inhale aerosol with one of two inhalation patterns, with a seven-day washout prior to testing with the other pattern. The two breathing patterns were as follows:

Breathing Pattern 1—Gently and fully exhale, followed by maximal inhalation within the flow limits indicated by a solid LED, followed by a 5 second breath hold. Exhale into filter. Repeat until end of dose is indicated.

Breathing pattern 2—Gently and fully exhale, inhaled through the inhaler for 5 sec, remove inhaler from mouth and inhale ambient air (chase air) for 1 sec, followed by 5 second breath hold. Exhale into the filter.

All subjects inhaled an aerosol of technetium labeled diethylenetriamine pente-acetic acid (99 mTc-DTPA) with an activity of 1 mCi and 0.9% saline solution in a total dose volume of 0.2 ml using a breath actuated vibrating mesh inhaler (Dance Biopharm, San Francisco, Calif.) which generates aerosol during inspiratory flow rates between 7 and 14 L/min, with a mean mass aerodynamic diameter (MMAD) ranging from 3.0-4.5 micron and geometric standard deviation of 2.0 as determined with a chilled next generation impactor (NGI). Immediately after nebulization was complete, radiation was counted with a scintillation camera (FORTE, Adac Laboratories, EUA) for 300 seconds, with a matrix of 256×256 in a view of posterior thorax, followed by a scan of the upper airway, and then device components (inhaler device, MPC and the filter into which subjects exhaled) to determine a mass balance of radioaerosol.

Analysis of radiolabeled aerosol deposited in the pulmonary and extra pulmonary compartments were expressed as a percentage of the total count. Left and right lung were delineated into regions of interest (ROI) on the horizontal (central, intermediate and peripheral) in accordance with previously reported methods. The ratio of peripheral and central counts were expressed as P/C ratio.

All subjects were asked for to express preference of the two breathing patterns.

Statistical analysis was carried out using SPSS 20.0 software (Statistical Package for the Social Sciences). The Shapiro-Wilk and Wilcoxon test were used. Group data were summarized using means and standard deviations. Differences between groups were evaluated by Mann Whitney test. All tests were conducted at a 95% confidence level and significance level of $p<0.05$.

Pattern 1, had a range of 10-20 sec inspiratory time, and trended towards higher lung dose with lower deposition in the mouthpiece than Pattern 2. The lung deposition with Pattern 1 was similar to prior in vitro findings with the Copley throat of 60-76%. Pattern 2 resulted in lower lung deposition and a 2 fold increase in the number of breaths required to complete the dose. The Peripheral to Central ratio of the right lung for all subjects trended higher with breathing Pattern 1 (2.49±0.6) than Pattern 2 (2.17±0.8).

Both breathing patterns were well tolerated, with subject preference for Pattern 1 as determined by questionnaire.

Figure 11:
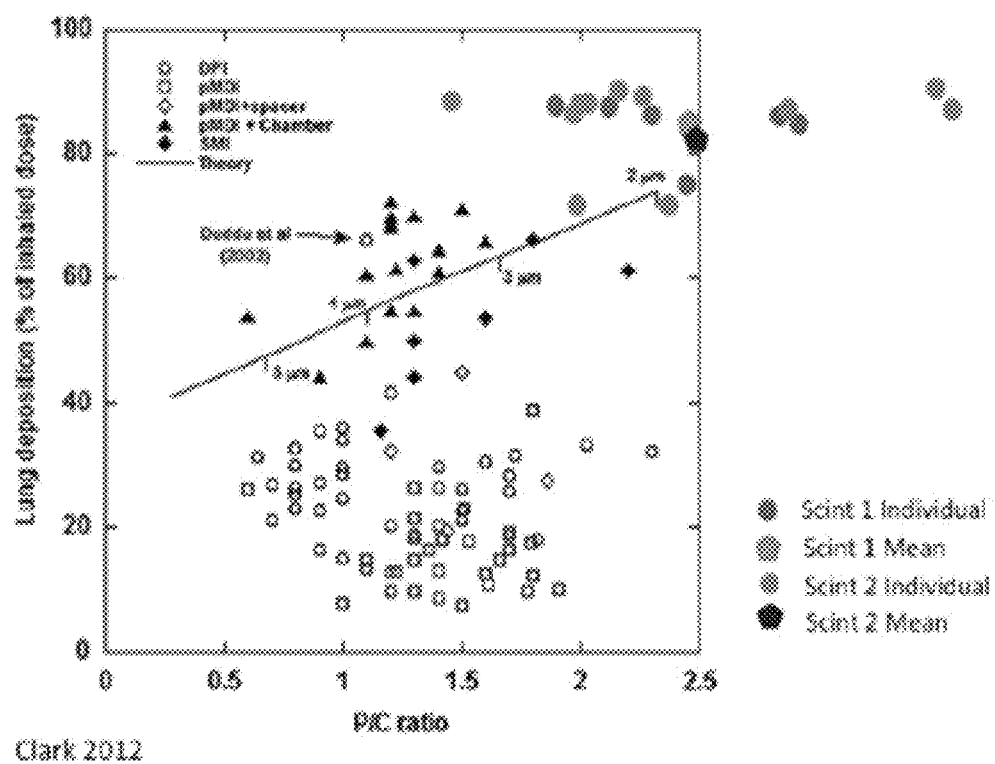
FIG. 11 shows experimental results of test of an inhaler embodying the invention, as overlaid on results of a previous comparative literature review.

The aerosol flow path design of aerosol emitted into the path of inhaled gas passing through the mouthpiece resulted in upper airway deposition of 9-12%. Other aspects of the performance of the system are represented in FIG. 11. FIG. 11 shows the performance of an inhaler embodying the invention as measured by the P/C ratio and lung deposition percentage, overlaid on data from a comparative literature review summarized in Clark (2012), Understanding Penetration Index Measurements and Regional Lung Targeting. *Journal of Aerosol Medicine and Pulmonary Drug Delivery,* 25(4), 179-187. In general, a higher P/C ratio and a higher lung deposition are desirable.

It will be apparent to those skilled in the art that various modifications and variations can be made in the method and system of the present invention without departing from the spirit or scope of the invention. Thus, it is intended that the present invention include modifications and variations that are within the scope of the appended claims and their equivalents.

What is claimed is:

1. A method of operating an inhaler, the method comprising:
    a) receiving a dose of liquid medicament onto a vibratable mesh;
    b) monitoring a flowrate of air flowing through the inhaler, the flow of air resulting from an inhalation by a user of the inhaler;
    c) actuating a vibratable element to vibrate the mesh, causing aerosolization of liquid medicament and creating a plume of aerosolized liquid medicament in the flowing air, wherein the plume of aerosolized medicament is made up of droplets having a mean mass aerodynamic diameter of between 3.5 and 5 microns, and wherein the plume of aerosolized medicament is supplied directly to a conduit through which the air flows through the inhaler, and the plume of aerosolized medicament is supplied through a side of the conduit;
    d) while less than substantially the entire amount of liquid medicament received onto the mesh has been aerosolized:
        1) when the flowrate is between a first threshold value and a second threshold value, continuing to vibrate the mesh and providing a first indication to the user of the inhaler indicating that the flowrate is in a desired range between the first and second threshold values;
        2) when the flowrate exceeds the second threshold value, stopping vibration of the mesh and providing a second indication to the user of the inhaler indicating that the flowrate is above the desired range;
        3) when the flowrate falls below the first threshold value during aerosolization of the liquid medicament, stopping vibration of the mesh and providing a third indication to the user of the inhaler indicating that the flowrate is below the desired range; and
    e) after substantially the entire amount of liquid medicament received onto the mesh has been aerosolized, providing a fourth indication to the user of the inhaler indicating that dosage is complete;
    wherein:
    the first indication is constantly-illuminated light of a first color, the second indication is light flashing at a first rate, the third indication is light flashing at a second rate slower than the first rate, and the fourth indication is light of a second color different from the first; and
    the conduit comprises a restrictor plate that is positioned upstream of the vibratable element such that the air flow in which the plume of aerosolized medicament is introduced is relatively laminar.

2. The method of claim 1, wherein the first threshold value is about 7 L/min and the second threshold value is about 14 L/min.

3. The method of claim 1, further comprising providing the third indication before the flowrate has reached the first threshold value.

4. The method of claim 1, wherein the first, second, third, and fourth indications are all provided by a single multicolor light emitting diode.

5. The method of claim 1, further comprising, when aerosolization of the dose of medicament is completed during an inhalation by the user of the inhaler, delaying the fourth indication.

6. The method of claim 5, wherein delaying the fourth indication comprises delaying the fourth indication until the end of the inhalation during which aerosolization of the dose of medicament is completed.

7. The method of claim 1, further comprising automatically shutting off the inhaler after the aerosolization of the dose of medicament is completed.

8. The method of claim 1, wherein more than one inhalation by the user of the inhaler is required to achieve aerosolization of substantially the entire dose of liquid medicament.

9. A method for operating an inhaler, the method comprising:
    a) receiving a dose of liquid medicament onto a mesh;
    b) monitoring a flowrate of air flowing through the inhaler, the flow of air resulting from an inhalation by a user of the inhaler;
    c) once the flowrate of air is between a first threshold value and a second threshold value, actuating a vibratable element to vibrate the mesh, causing aerosolization of liquid medicament from the liquid medicament dose and creating a plume of aerosolized liquid medicament in the flowing air, wherein the plume of aerosolized medicament is made up of droplets having a mean mass aerodynamic diameter of between 3.5 and 5 microns, and wherein the plume of aerosolized medicament is supplied directly to a conduit through which the air flows through the inhaler, and the plume of aerosolized medicament is supplied through a side of the flow channel;

d) subsequently, when the flowrate is between 7 L/min and 14 L/min, continuing to vibrate the mesh and constantly illuminating a light that is visible to the user of the inhaler; and when the flowrate exceeds 14 L/min, stopping vibration of the mesh and causing the light to flash, wherein:

the conduit comprises a restrictor plate that is positioned upstream of the vibratable element such that the air flow in which the plume of aerosolized medicament is introduced is relatively laminar.

10. The method of claim 9, further comprising:

when the flowrate falls below 7 L/min during aerosolization of the liquid medicament, stopping vibration of the mesh and causing the light to flash more slowly than when the flowrate is above 14 L/min.

11. The method of claim 10, further comprising:

after substantially the entire amount of liquid medicament received onto the mesh has been aerosolized, generating constantly-illuminated light of a different color than when the flowrate is between 7 and 14 L/min.

12. An aerosolization system, comprising:

a housing defining a mouthpiece and a liquid receptacle fluidly coupled to the mouthpiece, wherein the liquid receptacle defines an opening configured to receive a dosage of liquid medicament;

a conduit in the mouthpiece through which air inhaled by a user of the system flows when the user inhales through the mouthpiece;

a restrictor plate that is disposed within the conduit and that creates a relatively laminar flow from the inhaled air an aerosol generator disposed within the housing downstream of the restrictor plate, wherein the aerosol generator comprises:

a mesh; and a vibratable element configured to vibrate the mesh to turn the dosage of liquid into an aerosol, wherein the aerosol is made up of droplets having a mean mass aerodynamic diameter of between 3.5 and 5 microns, and wherein the aerosol is supplied directly to the relatively laminar flow within the conduit through a side of the conduit;

a flow sensor configured to monitor a flowrate of the air through the mouthpiece;

one or more lights visible to a user of the inhaler during use; and a controller coupled to the one or more lights, the flow sensor, and the vibratable element, wherein the controller is configured to:

a) once the flowrate of air is between a first threshold value and a second threshold value and while less than substantially the entire amount of liquid medicament received onto the mesh has been aerosolized:

1) when the flowrate is between a first threshold value and a second threshold value greater than the first, vibrate the mesh and provide a first indication using one of the one or more lights to the user of the inhaler indicating that the flowrate is in a desired range between the first and second threshold values;

2) when the flowrate exceeds the second threshold value, stop vibration of the mesh and provide a second indication using one of the one or more lights to the user of the inhaler indicating that the flowrate is above the desired range;

3) when the flowrate falls below the first threshold value during aerosolization of the liquid medicament, stop vibration of the mesh and provide a third indication using one of the one or more lights to the user of the inhaler indicating that the flowrate is below the desired range; and b) after substantially the entire amount of liquid medicament received onto the mesh has been aerosolized, provide a fourth indication to the user of the inhaler indicating that dosage is complete;

wherein the first threshold value is about 7 L/min and the second threshold value is about 14 L/min.

13. The aerosolization system of claim 12, wherein the first indication is a constantly-illuminated light of a first color, the second indication is a light flashing at a first rate, the third indication is a light flashing at a second rate slower than the first rate is, and the fourth indication is a light of a second color different from the first.

14. The method of claim 1, wherein step d) is performed throughout a maximal inhalation by the user.

15. The method of claim 14, wherein the maximal inhalation lasts between 10 and 20 seconds.

16. The method of claim 9, wherein step d) is performed throughout a maximal inhalation by the user.

17. The method of claim 16, wherein the maximal inhalation lasts between 10 and 20 seconds.

18. The method of claim 1, wherein the vibratable mesh is laterally offset and outside of an inner wall of the conduit.

19. The method of claim 1, wherein the vibratable mesh comprises a plurality of funneled shaped apertures that produce the droplets having a mean mass aerodynamic diameter of between 3.5 and 5 microns.

20. The method of claim 1, wherein the vibratable mesh produces the droplets at an output rate of between 0.4 mL/min and 0.6 mL/min.

* * * * *